United States Patent [19]

Smith, Jr.

[11] Patent Number: 4,482,775

[45] Date of Patent: Nov. 13, 1984

[54] ISOMERIZATION OF C₄ ALKENES

[75] Inventor: Lawrence A. Smith, Jr., Houston, Tex.

[73] Assignee: Chemical Research & Licensing Company, Houston, Tex.

[21] Appl. No.: 421,588

[22] Filed: Sep. 22, 1982

[51] Int. Cl.³ .......................... C07C 5/24; C07C 7/04
[52] U.S. Cl. ............................ 585/671; 203/DIG. 6; 203/28; 203/29; 203/38; 585/329; 585/510; 585/515; 585/668; 585/832; 585/921; 585/954
[58] Field of Search .................... 203/DIG. 6, 28, 29, 203/38; 585/329, 510, 515, 671, 668, 832, 921, 954

[56] References Cited

U.S. PATENT DOCUMENTS

| | | | |
|---|---|---|---|
| 3,629,473 | 12/1971 | Haunschild | 424/263 |
| 4,039,590 | 8/1977 | Ancillotti et al. | 585/864 |
| 4,198,530 | 4/1980 | Wentzheimer et al. | 568/697 |
| 4,215,011 | 7/1980 | Smith, Jr. | 203/DIG. 6 |
| 4,232,177 | 11/1980 | Smith, Jr. | 585/324 |
| 4,242,530 | 12/1980 | Smith, Jr. | 585/515 |
| 4,250,052 | 2/1981 | Smith, Jr. | 502/159 |
| 4,302,356 | 11/1981 | Smith, Jr. | 203/DIG. 6 |
| 4,307,254 | 12/1981 | Smith, Jr. | 203/DIG. 6 |
| 4,336,407 | 6/1982 | Smith, Jr. | 203/DIG. 6 |

Primary Examiner—Delbert E. Gantz
Assistant Examiner—A. Pal
Attorney, Agent, or Firm—Kenneth H. Johnson

[57] ABSTRACT

A method for isomerizing isobutene or n-butene to produce a mixture of isobutene and normal butene, and polymerizing at least a portion thereof to produce isobutene/n-butene codimer, which comprieses feeding at least 80 weight % of either the isobutene or n-butene to a catalytic distillation reactor containing a fixed bed acidic cation exchange resin catalyst packing which provides both the catalyst sites and distillation sites for the reaction products, isomerizing a portion of the isobutene or n-butene to produce a mixture of isobutene and n-butene and reacting at least a portion of the isobutene and n-butene to form codimer of isobutene and n-butene, whereby an overhead fraction containing any unreacted isobutene and n-butene and a bottoms fraction containing codimer is produced. The result of the reaction is substantially the same regardless whether the feed is isobutene or n-butene. Other aspects of the invention, include combinations of procedures to produce high purity isobutene and n-butene.

Either isobutene or n-butene product (depending on the desired product) can be recycled as feed, thus substantially carrying out the isomerization to extinction and total conversion to the desired product.

6 Claims, 1 Drawing Figure

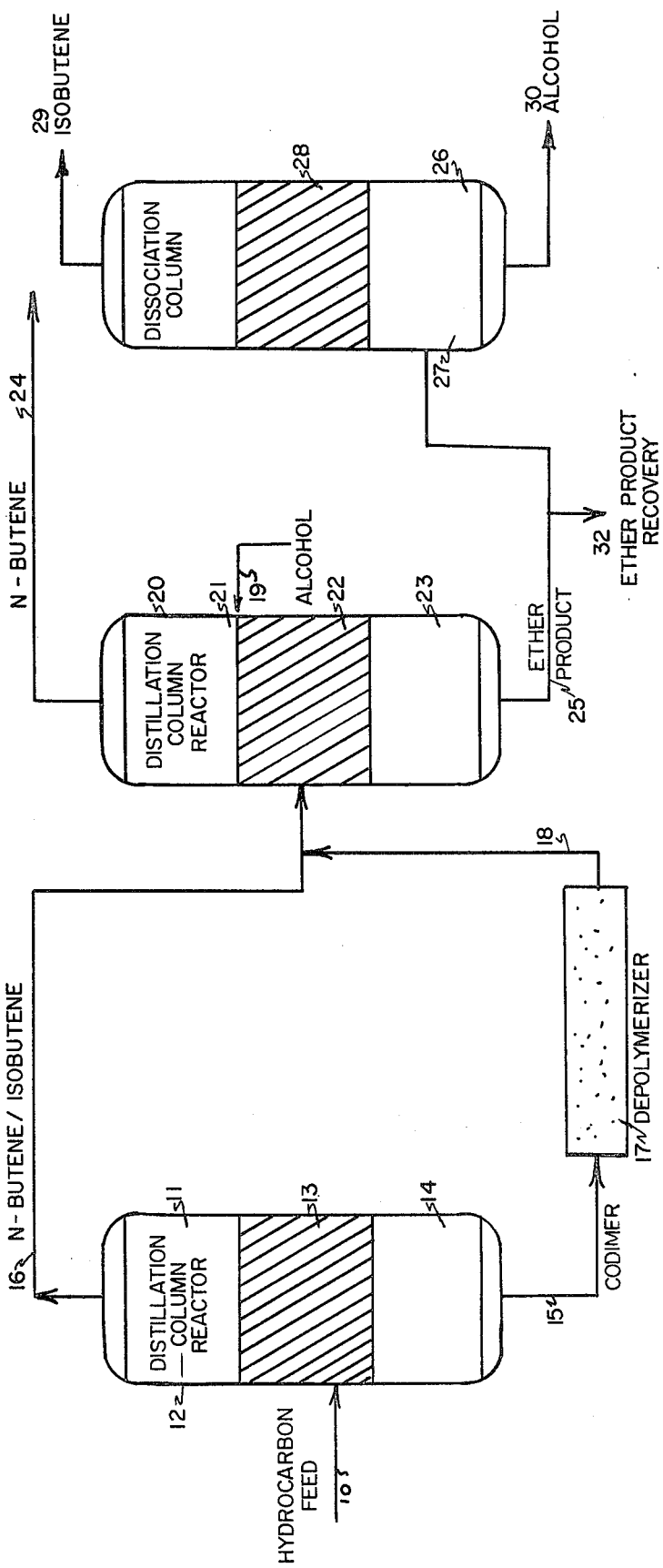

ISOMERIZATION OF C₄ ALKENES

The Government of the United States of America has certain rights in this invention pursuant to Contract No. DE-FC07-80CS40454 awarded by the U.S. Department of Energy.

BACKGROUND OF THE INVENTION

1. Field of the Invention

The present invention relates to a method of isomerizing n-butenes to isobutene or in the reverse reaction isobutene to normal butenes and the production of isobutene/n-butene codimer in a concurrent reaction distillation column reactor.

The process of concurrent reaction and distillation of the reaction catalyst as the distillation component is known as catalytic distillation and is described along with suitable catalyst structures in several commonly assigned U.S. patents and applications, including U.S. Pat. Nos. 4,215,011; 4,232,177; 4,242,530; 4,250,052; 4,302,356; 4,307,254 and 4,336,407.

Among the attributes of this process are:

(1) The utilization of a single reactor for carrying out the reaction and the initial distillation of the reaction mixture. Thus, initial investment in new equipment is substantially lower than liquid phase reactors and separate distillation towers. However, this aspect of the catalytic distillation gives rise to a further capital investment advantage in that the system can be retrofitted into existing distillation towers at a substantial savings in cost and time. This is an important consideration, since most refineries have unused or expendable distillation towers adequately suited for retrofitting.

(2) The catalytic reaction is very likely exothermic such as the etherifications and in those reactions where it is, the heat of reaction is used for the distillation (and supplemented by added heat as necessary).

(3) In exothermic reactions, the heat of reaction has been a problem, since in conventional reactions the heat must be dispersed or the reaction becomes a runaway, produces undesired by-products or certain types or catalyst can be damaged.

In the catalytic distillation, excess heat merely causes more boil-up and hence by controlling the pressure the temperature in the reactor is controlled and the heat of reaction is utilized as desired. Thus, in commercial scale the present process has proven very easy to start up, control and shut down. In other words, the reaction system has the ease and simplicity of operation of a distillation.

(4) The simultaneous reaction and distillation occurring within the catalyst structure results in disruption of reaction equilibrium and forces the reaction to completion.

It has now been found that the contact of isobutene with an acidic cation exchange resin catalyst result in the production of some n-butenes. Similarly, the contact of n-butenes (n-butene-1 and/or n-butene-2) results in the production of some isobutene. Since these are both reversible reactions they may or may not have occurred when mixed C₄ streams were contacted with the catalyst, that is the presence of the various isomers in the C₄ stream may surpress the isomerization or if it occurs, it is masked by the presence of the isomers.

In any event, the present invention provides the means to obtain the isomerization and recovery of the different isomers. The isobutene is important for the production of methyl tertiary butyl ether (gasoline octane improver), butyl rubber and the preparation of diisobutene which is used in detergent manufacture. The n-butenes are required in pure form for homopolymerization and as feeds for the oxidative production of butadiene.

SUMMARY OF THE INVENTION

Briefly stated the present invention is a process comprising feeding a C₄ alkene, either a normal butene or isobutene into a reactor wherein the catalyst structure serves as both the catalyst and as the distillation structure where at least a portion of the C₄ alkene is isomerized to its skeletal isomer, e.g., n-butene to isobutene or isobutene to n-butene and reacting a portion of the C₄ alkene with the isomer to form a codimer thereof. The codimer being a higher boiling material than either the feed or isomer, is recovered as a bottoms and any unreacted feed or isomer is recovered as an overhead. Since the isomerization is reversible, that is, it is equilibrium limited, the feed to the reaction should be predominantly the material to be isomerized or materials substantially inert in the reaction.

In one embodiment the present invention is a method for the isomerization of isobutene comprising:

(a) feeding a hydrocarbon stream wherein the predominant reactive hydrocarbon is isobutene to a distillation column reactor containing a fixed bed acidic cation exchange resin packing, (b) concurrently in said distillation column reactor
 (1) contacting said isobutene with said fixed bed to isomerize a portion thereof to form normal butenes,
 (2) reacting a portion of said normal butenes with a portion of said isobutene to form codimers, and
 (3) fractionating the resulting mixture, (c) withdrawing unreacted butenes as an overhead fraction at a point above said fixed bed, and (d) withdrawing said codimers as a bottoms product at a point below said fixed bed.

The feed stream may be further characterized in that the isobutene is substantially the only reactive component of the feed stream. Other olefins, particularly tertiary olefins should be excluded. Carries or diluents may be present. These are inerts and may be C₄ to C₁₀ alkanes.

The codimers may be depolymerized by contacting them with a bed of attapulgus clay to produce mixture of isobutene and n-butenes. This stream can subsequently be combined with the overhead and the combined streams treated to separate the isobutene and n-butenes or the dissociated stream can be separately treated.

The isobutene can be separated from the normal butenes by etherification as described in commonly assigned U.S. Pat. Nos. 4,307,253 and 4,336,407.

Briefly, the etherification process described there employs a distillation reaction system similar to that described herein where an alcohol, e.g., methanol is selectively reacted with isobutene producing an overhead substantially free of isobutene and a bottoms ether product. Liquid phase systems such as described in U.S. Pat. Nos. 3,629,478; 4,198,530 and 4,039,590 can also be used. The isobutene is preferentially and selectively reacted compared to the normal butenes.

Thus, the present product streams (overhead and dissociated streams) are easily treated according to the prior art etherification process to produce high purity normal butenes.

Another embodiment the present invention is a method the isomerization of n-butenes comprising:
 (a) feeding a hydrocarbon stream wherein the predominant reactive hydrocarbon is n-butene to a distillation column reactor containing a fixed bed acidic cation exchange resin packing,
 (b) concurrently in said distillation column reactor
  (1) contacting said n-butene with said fixed bed to isomerize a portion thereof to form isobutene.
  (2) reacting a portion of said normal butenes with a portion of said isobutene to form codimers and
  (3) fractionating the resulting mixture,
 (c) withdrawing unreacted isobutene and normal butenes as an overhead fraction at a point above said fixed bed, and
 (d) withdrawing said codimers as a bottoms product at a point below said fixed bed.

The feed stream may be further characterized in that the n-butenes are substantially the only reactive component of the feed stream. Olefins particularly the tertiary olefins should be excluded from this feed also. Carriers or diluents may be present, which are inerts, e.g., $C_4$ to $C_{10}$ alkanes.

BRIEF DESCRIPTION OF THE DRAWINGS

The FIGURE is a schematic representation of process for producing high purity isobutene and/or n-butene from an isomerization of either isobutene or n-butene.

DETAILED DESCRIPTION OF THE INVENTION

The reaction is reversible, as evidenced by the isobutene or n-butene feed producing the same type of products. In a catalytic distillation, i.e., the catalyst serves as a distillation component, the equilibrium is constantly disturbed, thus although the equilibrium constants for the isomerization of isobutene and n-butene may not be the same, the result because of the disruption of the equilibrium is substantially the same, i.e., an overhead consisting of isobutene and n-butenes and a bottoms product of isobutene/n-butene codimer. Small amounts of diisobutene are produced, as are some heavies which would indicate higher polymers, but there represent only a small portion of the total products.

The catalytic material employed in the isomerization must be in a form to serve as a distillation packing, for example, rings, saddles, balls, irregular pieces, sheets, tubes, spirals, packed in bags (as described in U.S. Pat. No. 4,242,530), plated on grills or screens, or reticulated polymer foams (the cellular structure of the foams must be sufficiently large so as not to cause high pressure drops through the columns or otherwise arranged, such as in chunks or concentric tubes to allow vapor flow). Broadly stated, the catalytic material is a component of a distillation system functioning as both a catalyst and distillation packing, i.e., a packing for a distillation column having both a distillation function and a catalytic function.

The reaction system can be described as heterogeneous since the catalyst remains as a distinct entity. The catalyst may be employed in such conventional distillation packing shapes as Raschig rings, Pall rings, saddles or the like. Similarly, the resin may be employed in a granular or bead form as described herein and the noted patents.

It has been found that the resin beads in a conventional fixed bed form too compact a mass for the upward flowing vapor and downward flowing liquid in a distillation system. However, it has been found that placing the resin beads into a plurality of pockets in a cloth belt, which is supported in the distillation column reactor by open mesh knitted stainless steel wire by twisting the two together, allows the requisite flows, prevents loss of catalyst, allows for the normal swelling of the beads and prevents the breakage of the beads through mechanical attrition. This novel catalyst arrangement is described in detail in commonly owned U.S. Pat. No. 4,242,530 which is incorporated herein.

The cloth may be of any material which is not attacked by the hydrocarbon feed or products or catalyst under the conditions of the reaction. Cotton or linen may be useful, but fiber glass cloth or "Teflon" cloth are preferred. Briefly, a preferred catalyst system comprises a plurality of closed cloth pockets arranged and supported in said distillation column reactor by wire mesh intimately associated therewith.

The particular catalytic material may be a powder, small irregular fragments or chunks, small beads and the like. The particular form of the catalytic material in the cloth pockets is not critical, so long as sufficient surface area is provided to allow a reasonable reaction rate. This sizing of catalyst particles can be best determined for each catalytic material (since the porosity or available internal surface area will vary for different materials and of course affects the activity of the catalytic material).

The present invention carries out the method in a catalyst packed distillation column which can be appreciated to contain a vapor phase and some liquid phase as in any distillation.

The success of the catalytic distillation approach lies in an understanding of the principles associated with distillation. First, because the reaction is occurring concurrently with distillation, the initial reaction products are removed from the reaction zone as quickly as formed. The removal minimizes chaining to form higher polymers. Second, because all the components are boiling, the temperature of the reaction is controlled by the boiling point of the mixture at the system pressure. The heat of reaction simply creates more boil up, but no increase in temperature. Third, the reaction has an increased driving force because the reaction products have been removed and can not contribute to a reverse reaction (LeChatelier's Principle).

As a result, a great deal of control over the rate of reaction and distribution of products can be achieved by regulating the system pressure. Also, adjusting the throughput (residence time = liquid hourly space velocity$^{-1}$) gives further control of product distribution and degree of isobutene or n-butene conversion.

The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa.

A reflux is preferably included in the system. The reflux ratio could vary over the rate of 0.5 to 20:1. In practice, the higher ratio may be used to compensate for a short catalyst bed such as required for experimental work. In commercial size units the catalyst bed would be provided so that lower reflux and hence higher unit productivity could be obtained at lower operating cost.

Catalysts suitable for the present process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C. and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferebly 1 to 20% by weight of the copolymer (see, for example, German Patent Specification No. 908,247).

The ion exchange resin is preferably used in a granular size of about 0.25 to 1 mm, although particles for 0.15 mm up to about 11 mm may be employed. The finer catalysts provide high surface area, but also result in high pressure drops through the reactor. The macroreticular form of these catalysts is preferred because of the must larger surface area exposed and the limited swelling which all of these resins undergo in a non-aqueous hydrocarbon medium.

Similarly, other acid resins are suitable, such as perfluorosulfonic acid resins which are copolymers of sulfonyl fluorovinyl ethyl and fluorocarbon and described in greater detail in DuPont "Innovation", Volume 4, No. 3, Spring 1973 or the modified forms thereof as described in U.S. Pat. Nos. 3,784,399; 3,770,567 and 3,849,243.

In addition to pockets of resin catalyst described, catalyst structures described in commonly owned U.S. Pat. No. 4,250,052 and copending U.S. patent application, Ser. No. 307,120, filed Sept. 30, 1981 which are incorporated herein, may be employed.

The hydrocarbon stream preferably contains at least 80 weight percent, more preferably at least 90 weight percent, of isobutene or n-butene and can be substantially pure isobutene or n-butene. Since the reaction is equilibrium limited, the greater the amount of one component (n-butene or isobutene) to the exclusion of the other, the greater the effectiveness of the process. In addition to the reactive components diluents may be present, preferably no more than 90% of the total feed will comprise diluents.

Although the basic feature of the present invention is the isomerization and production of the codimer, it would be likely and even desirable that the product streams were further treated to produce either high purity isobutene or high purity n-butenes.

The FIGURE is a schematic representation of a general process to produce high purity n-butene or isobutene employing the present isomerization as the central feature. The initial step is the feeding of an isobutene or n-butene feed 10 to a distillation column reactor 11 into a catalytic distillation section 13 which comprised of a plurality of the closed pocketed cloth bags wrapped about demister in a helical shape with each of the pockets containing Amberlyst 15 resin beads (Rohm & Haas Co., Phil. Pa.).

The exact location of the feed may vary but would generally be into the lower one third of the catalyst section so that the incoming feed would immediately contact the catalyst. The feed into the lower portion of the catalyst bed allows a longer contact time since both reactant feeds, i.e., isobutene and n-butenes will be carried out of column 11 as overhead. Regardless of which reactant is fed, i.e., isobutene or n-butene the isomerization reaction and the resultant products (although not necessarily the product ratios) are the same.

As the reactant feed contacts the catalyst it is isomerized to produce a mixture of isobutene and n-butenes, codimer of these two materials and some diisobutene. Sections 12 and 14 of the column are conventional distillation sections where the products are further fractionated. It should be appreciated that when the feed comprises isobutene, a large amount of isobutene is also produced. The dimer may be easily separated from the codimer by distillation or it can be depolymerized along with the codimer. Since the overall reaction is exothermic the heat of reaction is utilized in the fractionation and also dispersed thereby, i.e., excess heat of reaction, merely causes more boil up. An overhead 16 consisting of isobutene and n-butenes is produced. The n-butene and isobutene should be the lowest boiling components in the system, that is any diluent or inerts should have higher boiling points, since the overhead will necessarily be the lowest boiling material.

Although not shown, there could be draws streams at various points in the column to remove diluents or inerts to prevent their build up or they could be removed as a portion of the codimer bottoms product 15.

The codimer product is passed to depolymerizer 17 where it contacts attapulgus clay to produce about a 50/50 mixture of isobutene and n-butenes. In order to achieve the depolymerization the depolymerizer 17 is maintained at a temperature in the range 300° to 700° C. The dimer present is substantially depolymerized also. The isobutene/n-butene product 18 from the depolymerizer can now be combined with stream 16.

It is desirable to separate the isobutene/n-butene stream. However, because of the closeness of their boiling points this can not be done by simple distillation. In the past, the separation has been achieved by contacting the stream with sulfuric acid to thereby selectively remove isobutene. However, in commonly assigned U.S. Pat. Nos. 4,307,254 and 4,336,407, which are incorporated herein in their entirety, a better method for this procedure is disclosed, utilizing the catalytic distillation column and catalyst previously described for the isomerization wherein the combined n-butene/isobutene stream 16/18 is fed to a distillation column reactor 20 into a catalytic distillation section 20, generally in the lower portion of the bed while an alcohol, preferably a $C_1$ to $C_6$ monohydric alcohol 19 is fed into the upper end of the bed to obtain immediate contact of the isobutene and alcohol. The alcohol reacts preferably and selectively with the isobutene to form an ether which has a higher boiling point than the unreacted n-butene. The reaction product is fractionated within the catalyst section 22 and further within conventional distillation sections 21 and 23, with the ether being removed as a bottoms product 25 and the n-butene now freed of substantially all of the isobutene being removed as overhead 24.

Although the preparation of the ether is shown in a catalytic distillation reactor, it is not necessary that this method be used. A liquid phase system as shown in U.S. Pat. Nos. 3,629,478, 4,309,590 or 4,198,530 can be used with the appropriate distillation and water washing to separate n-butenes and isobutene ether and to remove alcohol.

If the alcohol is methanol or ethanol, there will be some of the alcohol azeotroped with the n-butenes and carried overhead. In that event a conventional water wash tower (not shown) may be used to remove the alcohol for reuse with the resultant product being high purity n-butenes. However, if the alcohol is a $C_3$ to $C_6$ monohydric alcohol an azeotrope with the n-butenes will not be formed and a high purity n-butene stream is directly produced as overhead 24.

If the hydrocarbon feed 10 were n-butenes, then stream 24 can be recycled to feed 10 with appropriate make up from other sources. However, if the desired product is n-butene, stream 24 is recovered.

The ether product 25 may be recovered as such, via 32, entirely or in part. Otherwise, all or a portion of the ether is fed to dissociation column 26 where the ether is vaporized and passed through dissociation section 28. This process is disclosed in commonly assigned U.S. patent application Ser. No. 363,053, filed Mar. 29, 1982, which is incorporated herein.

The dissociation section contains the same or a similar resin catalyst as previously described, which may be in the distillation structure used in columns 11 and 20. The product stream 29 from the dissociation column is primarily isobutene and the bottoms 30 are primarily alcohol.

Where the alcohol has $C_3$-$C_6$ carbon atoms the separation is effectively carried out by distillation, in the reactor distillation column, however, in the case of methanol and ethanol, a water wash (not shown) is best used, since the distillation will produce an isobutene-alcohol azeotrope. This high purity isobutene can be recovered if it is the desired product or if n-butenes are the desired product, the isobutene can be recycled to feed 10.

In this schematic representation, reboilers, reflux, trays, etc., are not depicted, but would be employed in an actual facility in the conventional and usual manner to optimize the performance and desired results.

As depicted a continuous stream process is shown, however, all of the reactions requiring a resin catalyst could be carried out in a single reactor in batch. The catalytic distillation is very easily started up and shut down thus changing the operation from isomerization to etherification or even dissociation is not costly, extremely time consuming or damaging to the catalyst.

The invention claimed is:

1. A method for producing high purity isobutene comprising:
    (a) feeding a hydrocarbon stream wherein the predominant reactive hydrocarbon comprises at least 80 weight percent n-butene to a distillation column reactor containing a fixed bed acidic cation exchange resin packing,
    (b) concurrently in said distillation column reactor:
        (1) contacting said n-butene with said fixed bed to isomerize a portion thereof to form a mixture of isobutene and n-butene,
        (2) reacting a portion of said normal butene with a portion of said isobutene to form codimer, and
        (3) fractionating the resulting mixture at a reflux ratio of 0.5 to 20:1,
    (c) withdrawing an overhead containing isobutene and n-butene at a point above said fixed bed,
    (d) withdrawing said codimer at a point below said fixed bed,
    (e) depolymerizing said codimer to produce an isobutene and n-butene stream,
    (f) contacting said depolymerized stream with an acidic cation exchange resin and an alcohol to selectively react said isobutene with said alcohol to form an ether,
    (g) separating said ether and unreacted n-butene by fractionation,
    (h) recovering an n-butene overhead,
    (i) recovering an ether bottoms product,
    (j) contacting said ether product in vapor phase with an acidic catalyst to dissociate said ether into isobutene and alcohol,
    (k) separating said alcohol and said isobutene and
    (l) recovering said isobutene.

2. The method according to claim 1 wherein said hydrocarbon stream is fed into said fixed bed acidic cation exchange resin packing.

3. The method according to claim 1 wherein steps (f–i) are carried out by feeding said depolymerized stream and an alcohol stream to a distillation column reactor containing a fixed bed acidic cation exchange resin packing; concurrently in said distillation column reactor:
    (1) contacting said depolymerized stream and said alcohol stream in said fixed bed to catalytically and selectively react said alcohol and isobutene to form ether,
    (2) fractionating the resulting mixture of ether and n-butene in said fixed bed, and
    (3) withdrawing ether from the distillation column reactor at a point below said fixed bed and withdrawing n-butene from the distillation column reactor at a point above said fixed bed.

4. The method according to claim 3 wherein said acidic catalyst in step (k) is an acidic cation exchange resin.

5. The method according to claim 4 wherein said alcohol is methanol or ethanol.

6. The method according to claim 4 wherein said alcohol is a $C_3$ to $C_6$ monohydric alcohol.

* * * * *